US011191735B2

(12) United States Patent
Komorowski et al.

(10) Patent No.: US 11,191,735 B2
(45) Date of Patent: Dec. 7, 2021

(54) ARGININE SILICATE FOR PERIODONTAL DISEASE

(71) Applicant: NUTRITION 21, LLC, Harrison, NY (US)

(72) Inventors: James R Komorowski, Trumbull, CT (US); Kazim Sahin, Elazığ (TR)

(73) Assignee: NUTRITION 21, LLC, Harrison, NY (US)

( * ) Notice: Subject to any disclaimer, the term of this patent is extended or adjusted under 35 U.S.C. 154(b) by 0 days.

(21) Appl. No.: 15/068,350

(22) Filed: Mar. 11, 2016

(65) Prior Publication Data
US 2016/0263135 A1 Sep. 15, 2016

Related U.S. Application Data

(60) Provisional application No. 62/133,076, filed on Mar. 13, 2015.

(51) Int. Cl.
| | |
|---|---|
| *A61K 31/695* | (2006.01) |
| *A61K 31/047* | (2006.01) |
| *A61K 9/00* | (2006.01) |
| *A61K 33/00* | (2006.01) |
| *A61K 31/198* | (2006.01) |

(52) U.S. Cl.
CPC .......... *A61K 31/047* (2013.01); *A61K 9/0063* (2013.01); *A61K 31/198* (2013.01); *A61K 33/00* (2013.01)

(58) Field of Classification Search
CPC .... A61K 31/047; A61K 33/00; A61K 31/198; A61K 9/0063; A61K 2300/00
See application file for complete search history.

(56) References Cited

U.S. PATENT DOCUMENTS

| | | | |
|---|---|---|---|
| 3,337,403 A | 8/1967 | Zentner | |
| 4,297,349 A | 10/1981 | Barcza | |
| 4,385,052 A | 5/1983 | Zackheim et al. | |
| 4,573,996 A | 3/1986 | Kwiatek et al. | |
| 4,597,961 A | 7/1986 | Etscorn | |
| 4,839,174 A | 6/1989 | Baker et al. | |
| 4,847,082 A | 7/1989 | Sabin | |
| 4,908,213 A | 3/1990 | Govil et al. | |
| 4,943,435 A | 7/1990 | Baker et al. | |
| 5,217,997 A | 6/1993 | Levere et al. | |
| 5,250,569 A | 10/1993 | Godfrey | |
| 5,284,657 A | 2/1994 | Lu et al. | |
| 5,288,497 A | 2/1994 | Stanley et al. | |
| 5,622,980 A | 4/1997 | Caldwell et al. | |
| 5,656,264 A | 8/1997 | Hanada et al. | |
| 5,662,920 A | 9/1997 | Santus | |
| 5,707,970 A | 1/1998 | McCarty et al. | |
| 5,716,610 A | 2/1998 | Jack et al. | |
| 5,763,392 A | 6/1998 | Hansen et al. | |
| 5,763,496 A | 6/1998 | Holland | |
| 5,804,203 A | 9/1998 | Hahn et al. | |
| 6,066,659 A | 5/2000 | Speck | |
| 6,123,936 A | 9/2000 | Platz et al. | |
| 6,132,394 A | 10/2000 | Lankinen | |
| 6,156,735 A | 12/2000 | McCarty et al. | |
| 6,182,655 B1 | 2/2001 | Keller et al. | |
| 6,298,847 B1 | 10/2001 | Datta et al. | |
| 6,344,444 B1 | 2/2002 | McCarty | |
| 6,387,394 B1 | 5/2002 | Baichwal et al. | |
| 6,418,926 B1 | 7/2002 | Chawla | |
| 6,462,051 B1 | 10/2002 | Nozawa et al. | |
| 6,803,456 B1 | 10/2004 | Kuhlmann | |
| 7,576,132 B2 | 8/2009 | Juturu et al. | |
| 2002/0068365 A1 | 6/2002 | Kuhrts | |
| 2003/0028169 A1 | 2/2003 | Fossel | |
| 2004/0009746 A1 | 1/2004 | Korman | |
| 2004/0097467 A1 | 5/2004 | Juturu et al. | |
| 2004/0204387 A1 | 10/2004 | McLaurin | |
| 2006/0204455 A1* | 9/2006 | Giniger | A61K 8/03 424/53 |
| 2007/0116831 A1* | 5/2007 | Prakash | A61K 8/602 426/548 |
| 2012/0141588 A1* | 6/2012 | Chopra | A61K 8/0241 424/489 |

(Continued)

FOREIGN PATENT DOCUMENTS

| | | |
|---|---|---|
| EP | 2805730 | 11/2014 |
| FR | 2745498 | 9/1997 |

(Continued)

OTHER PUBLICATIONS

Salt metathesis reaction—Wikipedia (Year: 2018).*
Geoffrey Stark, DDS (Year: 2018).*
Ask the Dentist (Year: 2018).*
Bassler, 1978, Hard water, food fibre, and silicon, British Medical Journal 1:919.
Bonnefont-Rkousselot (2002) Glucose and reactive oxygen species. Curr. Opin. Clin. Nutr. Metab. Care 5:561-568.
Calles-Escandon et al. "Diabetes and endothelial dysfunction: A clinical perspective." Endocrine Reviews. 22(1):36-52 (2001).

(Continued)

*Primary Examiner* — Sarah Pihonak
*Assistant Examiner* — Jason Deck
(74) *Attorney, Agent, or Firm* — Arnall Golden Gregory LLP

(57) ABSTRACT

Methods for treating and/or preventing periodontal disease with arginine silicate are disclosed. Methods may include the steps of identifying an individual in need of treatment for, or in need of prevention of, periodontal disease and administering an effective amount of an arginine-silicate complex to said individual. Arginine silicate may also be used to ameliorate one or more symptoms of periodontal disease. In some aspects, arginine silicate may be used to restore gum health and/or stop or reverse recession of the gums and/or the loss of gum tissue in the oral cavity.

6 Claims, 10 Drawing Sheets

(56) References Cited

U.S. PATENT DOCUMENTS

| | | | |
|---|---|---|---|
| 2016/0081959 A1 | 3/2016 | Bartos et al. | |
| 2017/0000809 A1 | 1/2017 | Komorowski | |
| 2017/0135969 A1 | 5/2017 | Komorowski | |

FOREIGN PATENT DOCUMENTS

| | | |
|---|---|---|
| FR | 2610522 | 8/1998 |
| WO | WO 98/34647 | 8/1998 |
| WO | WO 00/45651 | 8/2000 |
| WO | WO 02/28379 | 2/2003 |
| WO | WO-2004/017913 | 3/2004 |
| WO | WO-2012/173808 | 12/2012 |
| WO | WO-2017/004226 | 1/2017 |

OTHER PUBLICATIONS

Calver et al., 1992, Effect of local intra-arterial N.sup.G -monomethyl-L-arginine in patients with hypertension: the nitric oxide dilator mechanism appears abnormal, Journal of Hypertension 10:1025-1031.
Carlisle, 1972, Silicon: An Essential Element for the Chick, Science 178:619-621.
Carlisle, 1976, In vivo Requirement for Silicon in Articular Cartilage and Connective Tissue Formation in the Chick, J. Nutr. 106:478-484.
Carlisle, E.M. (1980) Biochemical and morphological change associated with long bone abnormalities in silicon deficiency. J. Nutr. 110:1046-1055.
Carlisle, et al. (1978) A requirement for silicon for bone growth in culture. Fed. Proc. 37:404.
Carlisle, et al. (1980) A silicon requirement for normal growth of cartilage in culture. Fed. Proc. 39:787.
Chen et al., 1991, L-Arginine Abrogates Salt-sensitive Hypertension in Dahl/Rapp Rats, J. Clin. Invest. 88:1559-1567.
Clarkson et al., 1996, Oral L-Arginine Improves Endothelium-dependent Dilation in Hypercholesterolemic Young Adults, J. Clin. Invest. 97(8):1989-1994.
Clowes et al., 1977, Suppression by heparin of smooth muscle cell proliferation in injured arteries Nature 265:625-626.
Cooke et al., 1994, Is NO an Endogenous Antiatherogenic Molecule Arteriosclerosis and Thrombosis 14(5):653-655.
Creager et al., 1992, L-Arginine Improves Endothelium-dependent Vasodilation in Hypercholesterolemic Humans J. Clin. Invest. 90:1248-1253.
Curtis, et al., Nitric oxide supplementation of synthesis of block-which is the better approach to treatment of heart disease?, Trends in Pharmacological Sciences 18(7):239-244 (1997).
Drexler et al., 1991, Correction of endothelial dysfunction in coronary microcirculation of hypercholesterolaemic patients by L-arginine, Lancet 338:1546-1550.
Edelman et al., 1990, Effect of controlled adventitial heparin delivery on smooth muscle cell proliferation following endothelial injury, Proc. Natl. Acad. Sci. USA 87:3773-3777.
Eisinger et al. (1993) Effects of silicon, fluoride, etidronate and magnesium on bone mineral density: a retrospective study. Magnisium Research. 6(3):247-249.
Garson et al., 1971, Organosilicon Entities as Prophylactic and Therapeutic Agents, Journal of Pharmaceutical Sciences 60(8):1113-1127.
Guyton et al., 1980, Inhibition of Rat Arterial Smooth Muscle Cell Proliferation by Heparin . . . , Circ. Res. 46:625-634.
Harrison's Principles of Internal Medicine, 13.sup.th edition, vol. 2, Isselbacher et al. (eds.), published 1994 by McGraw-Hill in 1994, p. 1321.
Hott et al. (1993) Short-term effects of organic silicon on trabecular bone in mature ovariectomized rats. Calcif. Tissue Int. 53:174-179.
Kelly et al. "Insulin resistance: lifestyle and nutritional interventions." Alternative Medicine Review. 5 (2):109-132 (2000).

Laurent et al., 1995, Dietary L-Arginine Attenuates Blood Pressure in Mineralocorticoid-Salt Hypertensive Rats, Clin. and Exper. Hypertension 17(7):1009-1024.
Loeper et al., 1978, The Physiological Role of the Silicon and its Antiatheromatous Action, in Biochemistry of Silicon and Related Problems, Bendz, G. et al. Eds., Plenum Press, NY 281-296.
Loeper et al., 1979, The Antiatheromatous Action of Silicon, Atherosclerosis 33:397-408.
Luscher, T.F., Endothelium-derived nitric oxide: The endogenous nitrovasodilator in the human cardiovascular system, Eur. Heart J., 12(Suppl. E):2-11 (1991).
Maulik, et al., Nitric Oxide signaling in ischemic heart, Cardiovasc. Res. 30(4):593-601 (1995).
McPherson et al. (2002) Superoxide activates constitutive nitric oxide synthase in a brain particulate fraction. Biochemical and Biophysical Research Communications. 296:413-418.
Miller, et al. "Practical Clinical Application of Biochemical Markers of Bone Turnover." Journal of Clinical Densitometry. 2(3):323-342 (1999).
Moncada et al., 1993, The L-Arginine-Nitric Oxide Pathway, The New England Journal of Medicine 329(27):2002-2012.
Parr, 1980, Silicon, Wine, and the Heart, Lancet p. 1087.
Proctor et al. "A novel complex of arginine-silicate improved micro and macrovascular function and inhibits glomerular sclerosis in insulin-resistant JCR:LA-cp rats." Diabetologia. 48(9):1925-1932 (2005).
Proctor et al. "Metabolic effects of a novel silicate inositol complex of the nitric oxide precursor arginine in the obese insulin-resistant JCR:LA-cp rat." Metabolism. 56(10):1318-1325 (2007).
Rubanyi, 1991, Endothelium-Derived Vasoactive Factors in Health and Disease, in Cardiovascular Significance of Endothelium-Derived Vasoactive Factors, Rubanyi, G.M., ed., Futura Publishing Company, Inc., NY xi-xix.
Schwarz et al., 1972, Growth-promoting Effects of Silicon in Rats, Nature 239:333-334.
Schwarz et al., 1977, Inverse Relation of Silicon in Drinking Water and Atherosclerosis in Finland, Lancet 538-539.
Schwarz, 1977, Silicon, Fibre, and Atherosclerosis, Lancet 454-457.
Schwarz, 1978, Significance and Functions of Silicon in Warm-Blooded Animals, in Biochemistry of Silicon and Related Problems, Bendz, G. et al. Eds., Plenum Press, NY 207-230.
Svehla, G., Reaction of Silicates, Vogels Textbook of Macro and Semimicro Qualitative Inorganic Analysis 5.sup.th Edition, Longman, London pp. 350-353 (1979).
Tsao, et al., Enhanced endothelial adhesiveness in hyperscolesterolemia is attenuated by L-arginine, Circulation 89(5):2176-2182 (1994).
Van Lente. "Markers of inflammation as predictors in cardiovascular disease." Clinica Chimica Acta. 293:31-52 (2000).
Wang et al. (1999) Effects of nitric oxide synthase inhibitors on systemic hypotension, cytokines and inducible nitric oxide synthase expression and lung injury following indotoxin administration in rats. J. Biomed. Sci. 6:28-35.
Toker et al., "The effects of hydrogen sulphide on alveolar bone loss in periodontitis," Minerva Stomatol, 2014; 63(4): pp. 103-110.
Partial European Search Report for European Application No. 03793307.4, dated Aug. 2, 2007.
Supplementary European Search Report for European Application No. EP 03793307.4 dated Dec. 4, 2008.
Schiffman et al., "Taste of nutrients: amino acids, vitamins and fatty acids," Perception & Physcophisics, 1975; 17(2): pp. 140-46.
U.S. Appl. No. 62/072,326, filed Oct. 29, 2014, Komorowski.
U.S. Appl. No. 62/254,314, filed Nov. 12, 2015, Komorowski.
U.S. Appl. No. 62/133,076, filed Mar. 13, 2015, Komorowski et al.
Ansel's Pharmaceutical Dosage Forms and Drug Delivery Systems, 8th Edition, Allen et al. eds., Lippincott Williams & Wilkins, Philadelphia, PA, 2005.
Asai et al., "Topical application of ex vivo expanded endothelial progenitor cells promotes vascularization and wound healing in diabetic mice," International Wound Journal, 2012: pp. 527-533.
Calles-Escandon et al., "Diabetes and endothelial dysfunction: A clinical perspective." Endocrine Reviews, 2001; 22(1): pp. 36-52.

(56) References Cited

OTHER PUBLICATIONS

Cherian et al., "L-arginine and Free Radical Scavengers Increase Cerebral Blood Flow and Brain Tissue Nitric Oxide Concentrations after Controlled Cortical Impact Injury in Rats," J. of Neurotrauma, 2003; 20(1): pp. 77-85.
Cosgrove, "Nitric Oxide Ingredients for Sports," Nutritional Outlook, [online], Nov. 8, 2013. Retrieved from the Internet: <URL: http://www.nutritionaloutlook.com/heart-health/nitric-oxide-ingredients-sports>.
Goodman and Gilman's: The Pharmacological Basis of Therapeutics, 8th Ed., Gilman et al., eds., Pergamon Press, Elmsford, NY, 1990.
Greenhalgh et al., "PDGF and FGF stimulate wound healing in the genetically diabetic mouse," American Journal of Pathology, 1990; 136(6):1235-1246.
International Search Report and Written Opinion dated Aug. 26, 2016 in PCT/US16/040128.
International Search Report and Written Opinion dated Jan. 27, 2020 in PCT/US19/58653.
Kelly et al., "L-Theanine and Caffeine in Combination Affect Human Cognition as Evidenced by Oscillatory alpha-Band Activity and Attention Task Performance," J. Nutr., 2008; 138(8): pp. 1572S-1577S.
Kottke et al., Chapter 10: Tablet Dosage Forms, in Modern Pharmaceutics, 4th Edition, Banker et al., eds., Marcel Dekker, Inc., New York NY, 2002: pp. 287-333.
Im-Emsap et al., Chapter 9: Disperse Systems, in Modern Pharmaceutics, 4th Edition, Banker et al., eds., Marcel Dekker, Inc., New York NY, 2002: pp. 237-285.
Marsh et al., "Relationships Among Balance, Visual Search, and Lacrosse-Shot Accuracy," J Strength Cond Res, 2010; 24(6): pp. 1507-1514.
Mind Lab Pro®, "Nootropics for Ganiers—Level Up Your Ganiing \Nith Cognitive Enhancers," Nootropics for Gamers—Level Up Your Gaming with Cognitive Enhancers, 2018, [online], [retrieved on Dec. 18, 2019]. Retrieved from the Internet: <URL: https://www.mindlabpro.com/blogs/nootropics/nootropics-gamers-gaming>.
Nutrition 21, Inc., EurekAlert!, [online], public release Dec. 13, 2007. Retrieved from the Internet: <URL: https://www.eurekalert.org/pub_releases/2007-12/n2-ncd121207.php>.
Pharmaceutical Dosage Forms: Tablets, Lieberman et al., eds., Marcel Dekker, Inc., New York, NY, 1989.
Rood-Ojalvo et al., "The benefits of inositol-stabilized arginine silicate as a workout Ingredient," Journal of the International Society of Sports Nutrition, 2015; 12(suppl. 1): p. 14.
Saul, [online], [retrieved on Nov. 27, 2017]. Retrieved from the Internet: <URL: <http://www.doctoryourself.com/fatigue.html>, 2005.
Schwarz, "Significance and Functions of Silicon in Warm-Blooded Animals, in Biochemistry of Silicon and Related Problems," Bendz, G. et al., Eds., Plenum Press, NY 207-230 (1978).
Schwarz, "Silicon, Fibre, and Atherosclerosis," Lancet, 1977; pp. 454-457.
Svehla, "Reaction of Silicates," Vogels Textbook of Macro and Semimicro Qualitative Inorganic Analysis 5th Edition, Longman, London, 1979; pp. 350-353.
Tsao et al., "Enhanced endothelial adhesiveness in hypercholesterolemia is attenuated by L-arginine," Circulation, 1994; 89(5): pp. 2176-2182.
Van Lente, "Markers of inflammation as predictors in cardiovascular disease," Clinica Chimica Acta., 2000; 293: pp. 31-52.
Wang et al. "Effects of nitric oxide synthase inhibitors on systemic hypotension, cytokines and inducible nitric oxide synthase expression and lung injury following indotoxin administration in rats," J. Biomed. Sci., 1999; 6: pp. 28-35.
Nitric Oxide Benefits, Supplements, Sources, and Side Effects, [online], [dated May 24, 2015]. Retrieved from the Internet: <URL: https://web.archive.org/web/20150524100645/http://www.nitricoxide.org: 80/>.
Nitrosigine Launch, [online], [dated May 16, 2013]. Retrieved from the Internet: <URL: https://nutrition21.com/nutrition-21-launches-nitrosigine-a-novel-patented-source-of-inositol-stabilized-arginine-silicate-accepted-by-the-fda-as-a-new-dietary-ingredient/>.
Wilson et al., "Impaired cognitive function and mental performance in mild dehydration," European Journal of Clinical Nutrition, 2003; 57(2): pp. S24-S29.

* cited by examiner

ARGININE SILICATE FOR PERIODONTAL DISEASE

CROSS-REFERENCE TO RELATED APPLICATIONS

This application claims priority to U.S. Provisional Patent Application No. 62/133,076, entitled "ARGININE SILICATE FOR PERIODONTAL DISEASE," filed Mar. 13, 2015, the entire content of which is hereby incorporated by reference.

BACKGROUND

1. Field

The present disclosure is related to the treatment and/or prevention of periodontal disease. More specifically, disclosed herein is the use of arginine silicate for the treatment and/or prevention of periodontal disease and associated symptoms.

2. Related Art

Periodontal disease, gum disease, periodontitis, and/or pyorrhea, refer to diseases affecting the periodontium and/or teeth. Periodontitis generally involves the progressive loss of the gum tissue and/or alveolar bone around the teeth.

SUMMARY

Some embodiments are directed to the use of arginine and silicate and/or inositol and/or complexes thereof for use in the treatment and/or prevention of periodontal disease. More particularly, some embodiments disclose that an arginine silicate complex may be used as dietary supplement to promote gum health, promote the soft tissue health of the oral cavity, treat or prevent periodontal disease, including, but not limited to, gingivitis, periodontitis, tooth decay, bone mineral density in the oral cavity and/or enamel erosion, and the like.

Symptoms of periodontitis include, but are not limited to, swollen gums, bright red or purplish gums, gums that feel tender when touched, gums that pull away from your teeth (recede), teeth that appear larger and/or longer than normal, increased space between teeth, pus around the teeth and/or gums, persistent bad breath, persistent bad taste in the oral cavity, one or more loose teeth, and/or a change in the way the teeth fit together during biting.

Some embodiments provide methods of promoting gum health, promoting the soft tissue health of the oral cavity, methods of treating or preventing gingivitis, treating or preventing periodontitis, treating or preventing tooth decay, improving bone mineral density in the oral cavity, and/or treating or preventing enamel erosion.

In some embodiments, the complex is provided to an individual in need thereof. In some embodiments, the complex is administered to an individual in need thereof. In some embodiments, the complex is provided or administered in an amount effective to improve gum health in an individual in need thereof. In some embodiments, the complex is provided or administered in an amount effective to promote gum health. In some embodiments, the complex is provided or administered in an amount effective to promote the health of the soft tissue of the oral cavity.

In some embodiments, the complex is provided or administered in an amount effective to treat periodontal disease. In some embodiments, the complex is provided or administered in an amount effective to prevent periodontal disease. In some embodiments, the complex is provided or administered in an amount effective to treat or prevent gingivitis. In some embodiments, the complex is provided or administered in an amount effective to treat or prevent periodontitis. In some embodiments, the complex is provided or administered in an amount effective to treat or prevent tooth decay. In some embodiments, the complex is provided or administered in an amount effective to treat or prevent decreased bone mineral density in the oral cavity.

In some embodiments, the effective amount is between about 100 mg and about 5,000 mg. In some embodiments, the effective amount is between about 250 mg and about 2,500 mg. In some embodiments, the effective amount is between about 500 mg and about 1,500 mg. In some embodiments, the complex is administered orally. In some embodiments, the complex is administered parenterally. In some embodiments, the complex is administered topically to the oral cavity. In some aspects, the complex is administered topically to the oral cavity in the form of a cream. In some aspects, the complex is administered topically to the oral cavity in the form of a paste (e.g., toothpaste).

Some embodiments provide methods of identifying an individual in need of an improvement in gum health, an improvement in the health of the soft tissue of the oral cavity, and/or an improvement in bone mineral density in the oral cavity. Some embodiments provide methods of identifying an individual in need of treatment for periodontal disease, gingivitis, periodontitis, tooth decay, and/or enamel erosion. Some embodiments provide methods of identifying an individual at risk for developing periodontal disease, gingivitis, periodontitis, tooth decay, and/or enamel erosion, (i.e., individuals in need of preventing the aforementioned conditions at a greater level than the general population).

In some embodiments, the complex is administered one to three times daily. In some embodiments, the complex is administered on a per-kilogram basis to humans or animals of different weights. For example, in some embodiments, the complex is administered one to three times daily in an amount ranging from about 2 mg/kg of body weight to 2,500 mg/kg of body weight.

Disclosed herein are methods for increasing bone density in the oral cavity, including, but not limited to alveolar bone and maxillary bone. The method may include identifying a patient having periodontal disease or symptoms thereof. The method may also include administering an amount of arginine silicate effective to increase bone density in the patient's oral cavity.

Methods for ameliorating one or more symptoms of periodontal disease and/or periodontitis are also disclosed. The method may include identifying a patient having periodontal disease or symptoms thereof. The method may also include administering an amount of arginine silicate effective to ameliorate the one or more symptoms.

Methods for reducing inflammation of the gums are also disclosed. The method may include identifying a patient having receding gums. The method may also include administering an amount of arginine silicate effective to reduce the patient's gum inflammation. The method may include administering an amount of arginine silicate effective to reduce, stop, or reverse gum tissue loss and/or gum recession.

Some embodiments provide methods of treating or preventing periodontal disease in an individual in need thereof comprising identifying an individual in need of treatment for, or in need of prevention of, periodontal disease, and administering an effective amount of an arginine-silicate complex to said individual.

Some embodiments provide methods for ameliorating one or more symptoms of periodontal disease comprising identifying an individual having periodontal disease or symptoms thereof, and administering an amount of arginine silicate effective to ameliorate the one or more symptoms.

Some embodiments provide methods of ameliorating gum tissue loss, comprising identifying an individual having receding gums; and administering an amount of arginine silicate effective to stop or reverse gum tissue loss.

In some embodiments, periodontal disease comprises tooth decay. In some embodiments, the periodontal disease comprises enamel erosion. In some embodiments, the periodontal disease comprises gingivitis. In some embodiments, the periodontal disease comprises decreased gum health.

In some embodiments, the effective amount of an arginine-silicate complex is administered orally. In some embodiments, the effective amount of an arginine-silicate complex is topically administered to the oral cavity. In some embodiments, the effective amount of an arginine-silicate complex is administered parenterally.

In some embodiments, the identifying an individual in need of treatment for, or in need of prevention of, periodontal disease comprises physical examination by a dental hygienist, dentist, oral surgeon, orthodontist, or medical doctor.

In some embodiments, the arginine-silicate complex comprises arginine, silicate, and inositol.

BRIEF DESCRIPTION OF THE DRAWINGS

While the experiments disclosed herein involve the treatment of rats, it is to be understood that the treatment of humans and other subjects is also contemplated. Moreover, various dosing amounts, schedules, formulations, and delivery systems are also fully contemplated.

DETAILED DESCRIPTION

Figure 1A:
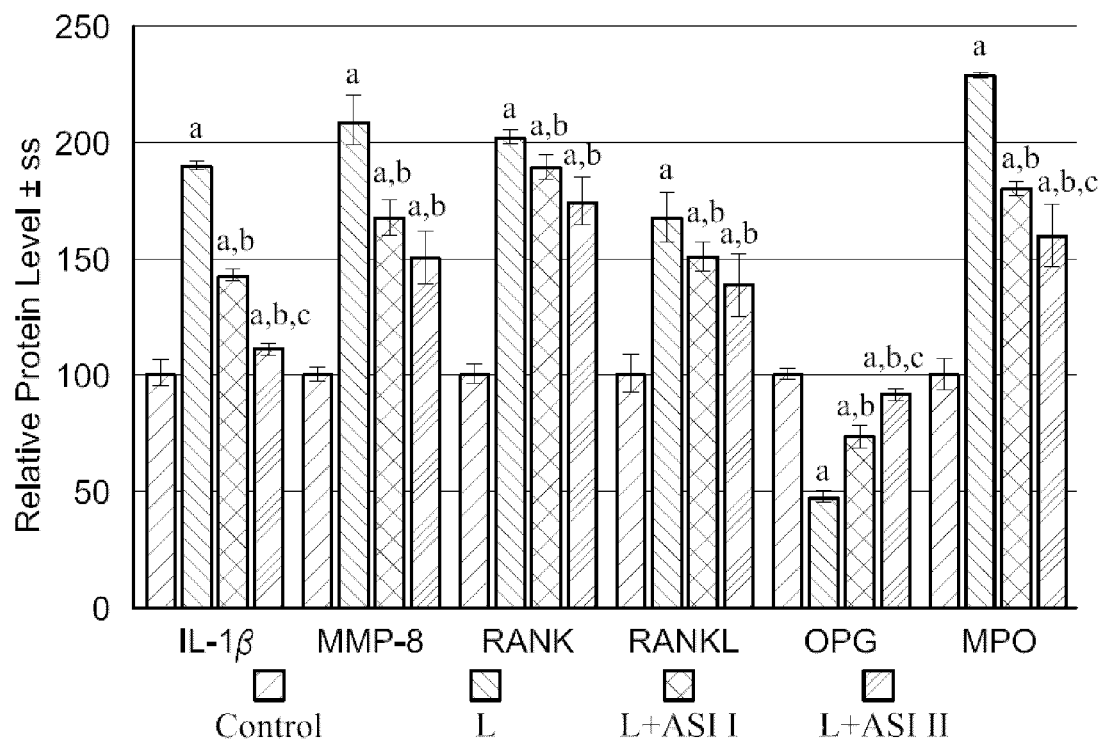
FIG. 1A graphically depicts the Il-1B, MMP-8, RANK, RANK-L, OPG and WO expression levels from periodontal tissue (a—significant differences from the group as control ($p<0.05$); b—significant differences from the group as periodontitis ($p<0.05$); c—significant differences from the group as ASI I ($p<0.05$)). No common superscript differs significantly at the level of $p<0.01$ by Fisher's multiple comparison test.
Figure 1B:
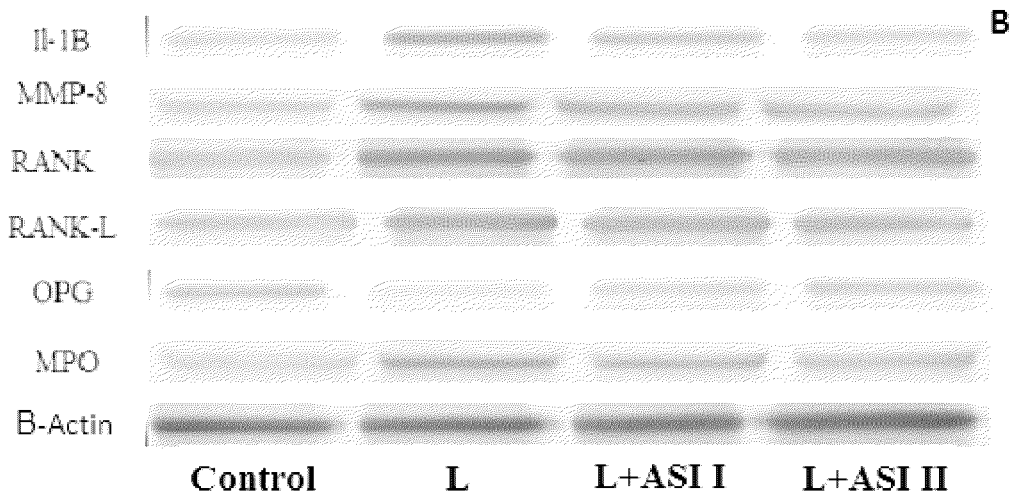
FIG. 1B depicts western blot strips Il-1B, MMP-8, RANK, RANK-L, OPG and MPO expression levels from periodontal tissue.

The present disclosure relates to new uses of an arginine silicate complex. In general, the complex is produced by combining arginine, a silicate salt and inositol. Although the compositions described herein generally contain arginine, silicate and inositol, it may be referred to throughout the specification as "arginine silicate," "arginine silicate inositol," "ASI," or "complex."

The complexes of the present disclosure may comprise and/or consist essentially of ASI for use in the treatment and/or prevention of periodontal disease. In some aspects, the present compositions may be used to ameliorate one or more biochemical markers of one or more disease states associated with periodontal disease. In some aspects, methods disclosed herein include administering to a subject a dose of a composition containing an arginine silicate inositol complex that is effective to treat and/or ameliorate one or more systems associated with periodontal disease Some embodiments provide a method for ameliorating the symptoms associated with a bone or cartilage disorder in the oral cavity of an individual in need thereof, comprising administering to the individual an effective amount of the arginine silicate inositol complex. In some aspects, the disclosed complexes may be used to decrease inflammation of the gums. For example, in some aspects, arginine silicate can be used to reduce inflammatory cell infiltration in periodontal tissue. In some aspects, arginine silicate can be used to slow the rate of lacunae resorption. In some aspects, arginine silicate can be used to decrease the length of the distance between the mesial cemento-enamel junction and the mesial crestal bone in patients in need thereof. In some aspects, arginine silicate can be used to decrease the length of the distance between the roof of furcation crestal bone and the roof of furcation. Arginine silicate may also be used to promote gum growth such that the cementoenamel junction of a tooth is no longer exposed.

In some embodiments, an individual is a mammal. In some embodiments, the mammal is a human. In some embodiments, the mammal is mouse, rat, dog, cat, or equine.

In some aspects, the disclosed complexes may be used to decrease the amounts of one or more biomarkers associated with periodontitis.

The compositions of the present disclosure may comprise and/or consist essentially of ASI for use in the treatment and/or prevention of tooth decay. In some aspects, arginine silicate can be used to increase bone density in the oral cavity and/or prevent the loss of bone mass in the oral cavity. In some aspects, the arginine silicate can be used to increase tooth strength and/or enamel levels. In some aspects, the arginine silicate can be used to prevent and/or reduce the rate of bone resorption in the oral cavity.

Some embodiments may be administered parenterally, orally, intravenously, intraarterially, intramuscularly, topically, or in any other systemic or localized fashion, in appropriate dosage units, as desired.

The term "parenteral" used herein includes subcutaneous, intravenous, intraarterial, injection or infusion techniques, without limitation. However, oral administration is preferred, including topical administration to the oral cavity (e.g., as a mouthwash or mouth rinse). Some embodiments may be in a powder form, liquid form or a combination of powder and liquid forms. For oral administration, the complexes may be provided as a tablet, aqueous or oral suspension, dispersible powder or granule, emulsion, hard or soft capsule, syrup or elixir.

Compositions intended for oral use may be prepared according to any method known in the art for the manufacture of pharmaceutical compositions and such compositions may contain one or more of the following agents: sweeteners, flavoring agents, coloring agents, preservatives, solubilizers, wetting agents, stabilizers, colorants, antioxidants, coating agents and diluents. The sweetening agents and flavoring agents will increase the palatability of the preparation. Tablets containing silicate inositol in an admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Formulations for oral use may also include solutions and/or suspensions. Liquid formulations may be provided. In some aspects, the formulations may include a mouthwash or mouth rinse.

In some aspects, arginine silicate may be added to food that is designed for animals. For example, the formulation may be added to and/or comprise a pet treat or biscuit, for example, a dog biscuit or a cat treat Aqueous suspensions may contain the complexes disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Oil suspensions may be formulated by suspending the active ingredient as a dispersible powder or granule in water, in an admixture with a dispersing or wetting agent, a suspending agent and one or more preservatives. Additional excipients, for example sweetening, flavoring and coloring agents, may also be present. Syrups and elixirs may be formulated with sweetening agents such as glycerol, sorbitol or sucrose. Such formulations may also include a demulcent, a preservative, a flavoring or a coloring agent.

In some embodiments, the complexes are administered as a composition comprising an orally acceptable carrier in a product such as mouthwash, toothpaste, dental cream, chewing gum, denture adhesive, or a soft pliable tablet ("chewie"). As used herein, an "orally acceptable carrier" refers to a material or combination of materials that are safe for use in the compositions disclosed herein, commensurate with a reasonable benefit/risk ratio.

The compositions for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in injectable preparations.

The disclosed complexes can also be administered by inhalation. In this administration route, an arginine silicate inositol complex can be dissolved in water or some other pharmaceutically acceptable carrier liquid for inhalation, or provided as a dry powder, and then introduced into a gas or powder that is then inhaled by the patient in an appropriate volume so as to provide that patient with a measured amount of an arginine silicate inositol complex.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the arginine silicate inositol complex. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein an arginine silicate inositol complex is dissolved in an aqueous constituent to gradually release over time, can be prepared by copolymerization of hydrophilic mono-olefinic monomers such as ethylene glycol methacrylate. Matrix devices, wherein an arginine silicate inositol complex is dispersed in a matrix of carrier material, can be used. The carrier can be porous, non-porous, solid, semi-solid, permeable or impermeable. Alternatively, a device comprising a central reservoir of an arginine silicate inositol complex surrounded by a rate controlling membrane can be used to control the release of the complex. Rate controlling membranes include ethylene-vinyl acetate copolymer or butylene terephthalate/polytetramethylene ether terephthalate. Use of silicon rubber depots are also contemplated.

Controlled release oral formulations are also well known. In one embodiment, the active complex is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process. In a preferred embodiment, transdermal patches, steady state reservoirs sandwiched between an impervious backing and a membrane face, and transdermal formulations, can also be used to deliver an arginine silicate inositol complex. Transdermal administration systems are well known in the art. One type of transdermal patch is a polymer matrix in which the active agent is dissolved in a polymer matrix through which the active ingredient diffuses to the skin.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

The term "treating" or "treatment" does not necessarily mean total cure. Any alleviation of any undesired signs or symptoms of the disease to any extent or the slowing down of the progress, or even prevention of the disease or condition can be considered treatment.

As used herein, a composition that "substantially" comprises a complex means that the composition contains more than about 80% by weight, more preferably more than about 90% by weight, even more preferably more than about 95% by weight, and most preferably more than about 97% by weight of the complex.

Throughout the specification there are references, for example, to identifying a subject in need of administration of a ASI or in need of treatment for periodontal disease and the like or in need of prevention of periodontal disease and the like. The term identification is not intended to be limiting and includes in each instance a belief by the subject that the composition will benefit the subject, self-identification, and identification by third party using various techniques. The identification may include, but is not limited to, the association or identification with one or more conditions selected from the group consisting of: periodontal disease, gingivitis, gum disease, tooth decay, gum recession, periodontitis, enlarged gum pockets, swollen gums, bleeding gums, loose teeth, sensitive teeth, persistent bad breath, and/or poor oral hygiene. Identification may include physical examination by a dental hygienist, dentist, oral surgeon, orthodontist, or medical doctor. In some aspects, individuals may self-identify.

The amount of a complex that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges.

The precise dose to be employed in the compositions will also depend on the route of administration, and the seriousness of the disease or disorder, and should be decided according to the judgment of the practitioner and each circumstances. However, suitable dosage ranges for oral administration are generally about 0.001 milligram to 5000 milligrams of a total ASI per kilogram body weight. In preferred embodiments, the oral dose is 0.01 milligram total ASI complex to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. Oral compositions preferably contain 10% to 95% active ingredient.

Advantageously, an effective amount may be between about 2 mg and about 2,500 mg. More advantageously, the effective amount is between about 500 mg and about 1,000 mg. For the average 70 kg man, this may equate to a dosage of between about 3.6 and 14 mg/kg (250-2,500 mg) and between about 7.1 mg/kg and 14 mg/kg (500 mg-1,000 mg), respectively. Effective doses may be extrapolated from dose-response curves derived from in vitro or animal model test systems. Such animal models and systems are well known in the art.

The compositions disclosed herein can preferably be formulated with other active ingredients. For example, compositions disclosed herein may be formulated in combination with fluoride. The transitional phrase "consisting essentially of" limits the scope of a claim to the specified materials or steps and those that do not materially affect the basic and novel characteristics of the claimed invention. Thus, for example, a composition consisting essentially of arginine silicate would not include other ingredients that are known to treat and/or prevent periodontal disease (e.g. fluoride).

The complexes may be administered once or twice a day. In some aspects, the complexes are administered three times a day. For example, the complexes may be administered before, after, or during a meal. In some aspects the complexes are administered before, during, or after tooth brushing.

EXAMPLES

Example 1

All animals and surgical procedures were handled in accordance with guidelines of the Chancellor's Animal Research Committee of the Office for Protection of Research Subjects at the University of Inonu, Malatya, Turkey (2013/A-12). Fifty-two (2-month-old) female Sprague-Dawley rats weighing 138 (Experimental Research Center of Inonu University) were kept in temperature-controlled cages (approximately 25° C.), exposed to a 24-hr light-dark cycle of equal time, and had free access to water and food ad libitum.

The fifty-two rats were randomly divided into four groups: the non-ligated treatment (Control) group (n=13), the ligature-only (L) group (n=13), the ligature plus ASI ("arginine-silicate-inositol;" Nutrition 21, NY, USA, see, e.g. U.S. Pat. Nos. 5,707,970 and 7,576,132) with dose of 1.81 mg/kg of diet group (designated "ASI I"), (n=13), the ligature plus ASI with dose of 3.62 mg/kg of diet group (designated "ASI II") (n=13).

For all the studies described herein, the well-characterized ligature model of placing a sterile wire ligature around the crown of the right first maxillary molar was utilized. Rats were anesthetized with Rompun®, 10 mg/kg ve Xylazine®, 40 mg/kg ketamin, and a sterile 28-gauge wire ligature was placed around the cervical portion of the right first molar. Animals continued to receive basal diet or basal diet supplemented with 1.81 or 3.62 g ASI/kg diet (Proctor et al., 2005) for 8 weeks before ligature placement.

Animals were monitored weekly to ensure presence of the ligature, and the ligature was adjusted if necessary. At the end of the experiment, animals were euthanized, blood was collected via cardiac puncture, and serum biomarkers including Ca, Mg, phosphorus, alkaline phosphatase, and CRP (C-reactive protein) were measured. Whole maxillas were removed, placed in 10% formalin for 48 hours, and stored in 70% ethanol.

A histologic evaluation was performed by a single examiner (I.O.) who was masked to the identity of the samples. The specimens were fixed in a 10% neutral-buffered formalin solution and demineralized in an aqueous 10% formic acid solution. The specimens were then dehydrated, embedded in paraffin, and sectioned along the molars in a mesio-distal plane for hematoxylin and eosin staining, as described by Toker et al. Light microscopy (Nikon, Tokyo, Japan), and assessment was performed on the two sections with a thickness of about 6 mm, corresponding to the buccal and lingual areas between the first and second molars where ligatures had been placed.

The areas of alveolar bone and interdental septum were analyzed under light microscopy, considering parameters including inflammatory cell infiltration ("ICI") of the periodontal tissues, existing resorption lacunae (osteoclast surfaces), osteoblastic activity (forming surfaces) and the number of osteoclasts. ICI was determined by semiquantitative scoring as not visible ICI (score=0), slightly visible ICI (score=1), and dense ICI (score=2). Osteoclasts were counted based on their morphology.

Bones were imaged by micro-computed tomographic (μCT) scanning (SkyScan1172 Compact MKT (Kontich, Belgium)) at 16-μm resolution, and volumetric data were converted to DICOM format and imported in the Recon 1.6.9.4 SkyScan (Contich, Belgium) to generate 3D and multiplanar reconstructed images. An oral and maxillofacial radiologist (ST), blinded to the specific animal treatment, evaluated the μCT images of all animals to identify and score bony changes and performed all linear measurements using Recon software tools.

To quantify the amount of bone loss induced by experimental periodontal disease (PD), the imaged volume was oriented with the nasal cavity floor parallel to the horizontal plane and the midpalatal suture parallel to the midsagittal plane. Then the volume was angled such that the long axis of the distal root of the first molar (D1) and the mesial root of the second molar (M2) were vertical to the horizontal plane. Then the distance between the cementoenamel junction (CEJ) and the alveolar bone crest (ABC) was measured at the center of D1 and M2. To quantitatively assess changes in the width of the buccal alveolar outline on axial slices, the imaged volume was oriented such that the floor of the nasal cavity was parallel to the horizontal plane and the midpalatal suture was parallel to the midsagittal plane. Then the shortest distance from the buccal surface of the root to the buccal outline of the alveolar ridge was measured for the mesial and distal roots of the first and second molars at the level of the hard palate.

The results are summarized in the tables below.

Results

TABLE 1

The effects of ASI on serum parameters

|  | CONTROL | L | L + ASI I | L + ASI II | P |
|---|---|---|---|---|---|
| ALP (U/L) | 410.29 ± 162.44 | 323.77 ± 124.98 | 440.31 ± 69.93 | 380.54 ± 85.36 | 0.061 |
| P (mg/dl) | 7.69 ± 1.65 | 7.98 ± 1.59 | 8.35 ± 1.82 | 7.82 ± 1.61 | 0.813 |
| Ca (mg/dl) | 9.66 ± 1.17 | 10.17 ± 0.57 | 10.37 ± 0.32 | 9.78 ± 0.66$^c$ | 0.050* |
| CRP (mg/dl) | 0.13 ± 0.05 | 0.26 ± 0.05$^a$ | 0.16 ± 0.07$^b$ | 0.18 ± 0.06$^b$ | 0.001** |

Control: the nonligated treatment.

L: the ligature-only;

L + ASI I: the ligature plus ASI with dose of 1.81 mg/kg of diet.

L + ASI II; the ligature plus ASI with dose of 3.62 mg/kg of diet.

*$p < 0.05$, **$p < 0.01$.

$^a$Significant differences from the group as control ($p < 0.05$).

$^b$Significant differences from the group as periodontitis ("L") ($p < 0.05$).

$^c$Significant differences from the group as ASI I ($p < 0.05$).

TABLE 2

The effects of ASI on several protein levels

|  | CONTROL | L | L + ASI I | L + ASI II | P |
|---|---|---|---|---|---|
| IL-1β | 100 ± 5.24 | 189.82 ± 1.84$^a$ | 142.5 ± 2.53$^{a,b}$ | 111.24 ± 2.35$^{a,b,c}$ | 0.016* |
| MMP-8 | 100 ± 2.72 | 208.72 ± 11.14$^a$ | 166.79 ± 7.86$^{a,b}$ | 150.256 ± 11.6$^{a,b}$ | 0.019* |
| RANK | 100 ± 4.31 | 202.18 ± 2.83$^a$ | 189.27 ± 5.3$^{a,b}$ | 174.31 ± 9.82$^{a,b}$ | 0.023* |
| RANKL | 100 ± 8.06 | 167.06 ± 10.72$^a$ | 150.11 ± 6.34$^{a,b}$ | 138.35 ± 13.6$^{a,b}$ | 0.022* |
| OPG | 100 ± 2.3 | 47.25 ± 2.33$^a$ | 72.87 ± 4.67$^{a,b}$ | 91.13 ± 3.04$^{a,b,c}$ | 0.016* |
| MPO | 100 ± 6.9 | 228.86 ± 1.13$^a$ | 180 ± 2.97$^{a,b}$ | 159.59 ± 13.09$^{a,b,c}$ | 0.016* |

Control: the nonligated treatment.
L: the ligature-only.
L + ASI I: the ligature plus ASI with dose of 1.81 mg/kg of diet.
L + ASI II: the ligature plus ASI with dose of 3.62 mg/kg of diet.
IL-1β: Interleukin 1β.
MMP-8: Matrix Metalloproteinases-8.
RANK: Receptor Activator of Nuclear Factor kappa β.
RANKL: Receptor Activator of Nuclear Factor kappa β Ligan.
OPG: Osteoprotegerin.
MPO: Myeloperoxidase.
*p < 0.05.
$^a$Significant differences from the group as control (p < 0.05).
$^b$Significant differences from the group as periodontitis ("L") (p < 0.05).
$^c$Significant differences from the group as ASI I (p < 0.05)

Table 1 shows that serum CRP levels in ASI treatment groups were significantly lower in comparison to the induced periodontitis group. Serum calcium levels were also significantly reduced in the ASI II group.

Table 2 shows that serum levels for IL-1β, MMP-8, RANK, RANKL, OPG, MPO were significantly lower in comparison to the periodontitis group. Serum levels for IL-1β and MPO in the ASI II group were significantly lower in comparison to the ASI I group. The results of Table 2 are graphically depicted in FIG. 1A.

TABLE 3

Inflammatory cell infiltration (ICI).

| ICI | CONTROL n (%) | L n (%) | L + ASI I n (%) | L + ASI II n (%) | P |
|---|---|---|---|---|---|
| Little visible | 9 (%69.2) | 0 (%0) | 0 (%0) | 0 (%0) | 0.001** |
| Slightly visible | 4 (%30.8) | 3 (%23.1) | 9 (%69.2) | 11 (%84.6) |  |
| Dense | 0 (%0) | 10 (%76.9) | 4 (%30.8) | 2 (%15.4) |  |

Control: the nonligated treatment.
L: the ligature-only.
L + ASI I: the ligature plus ASI with dose of 1.81 mg/kg of diet.
L + ASI II: the ligature plus ASI with dose of 3.62 mg/kg of diet.
**p < 0.01

Figure 2:
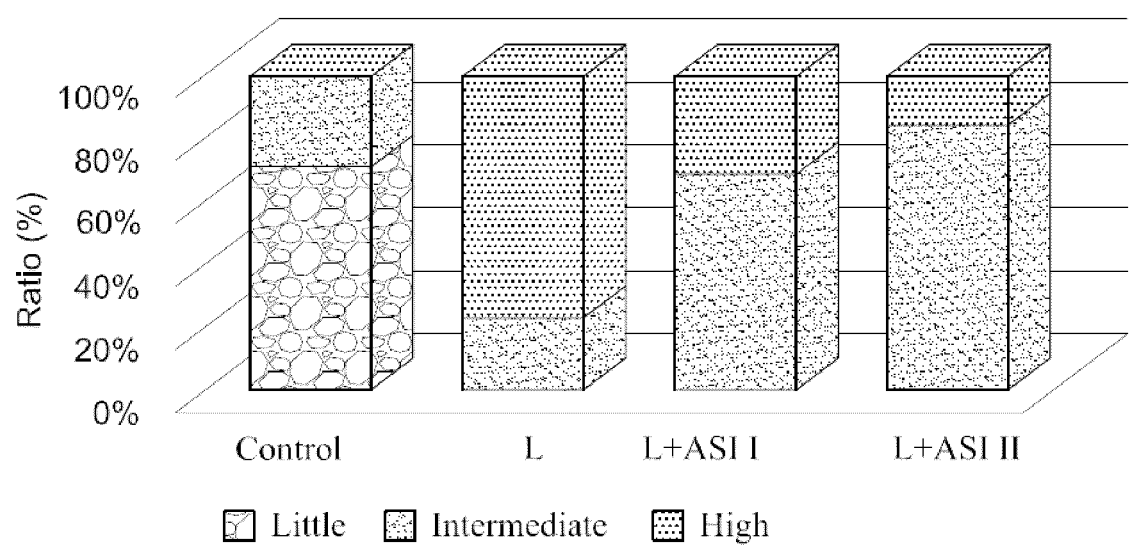
FIG. 2 graphically depicts inflammatory cell infiltration ("ICI") levels for different treatment populations.

Table 3 shows that ICI was significantly reduced by ASI treatment. The results of Table 3 are graphically depicted in FIG. 2.

Figure 3:
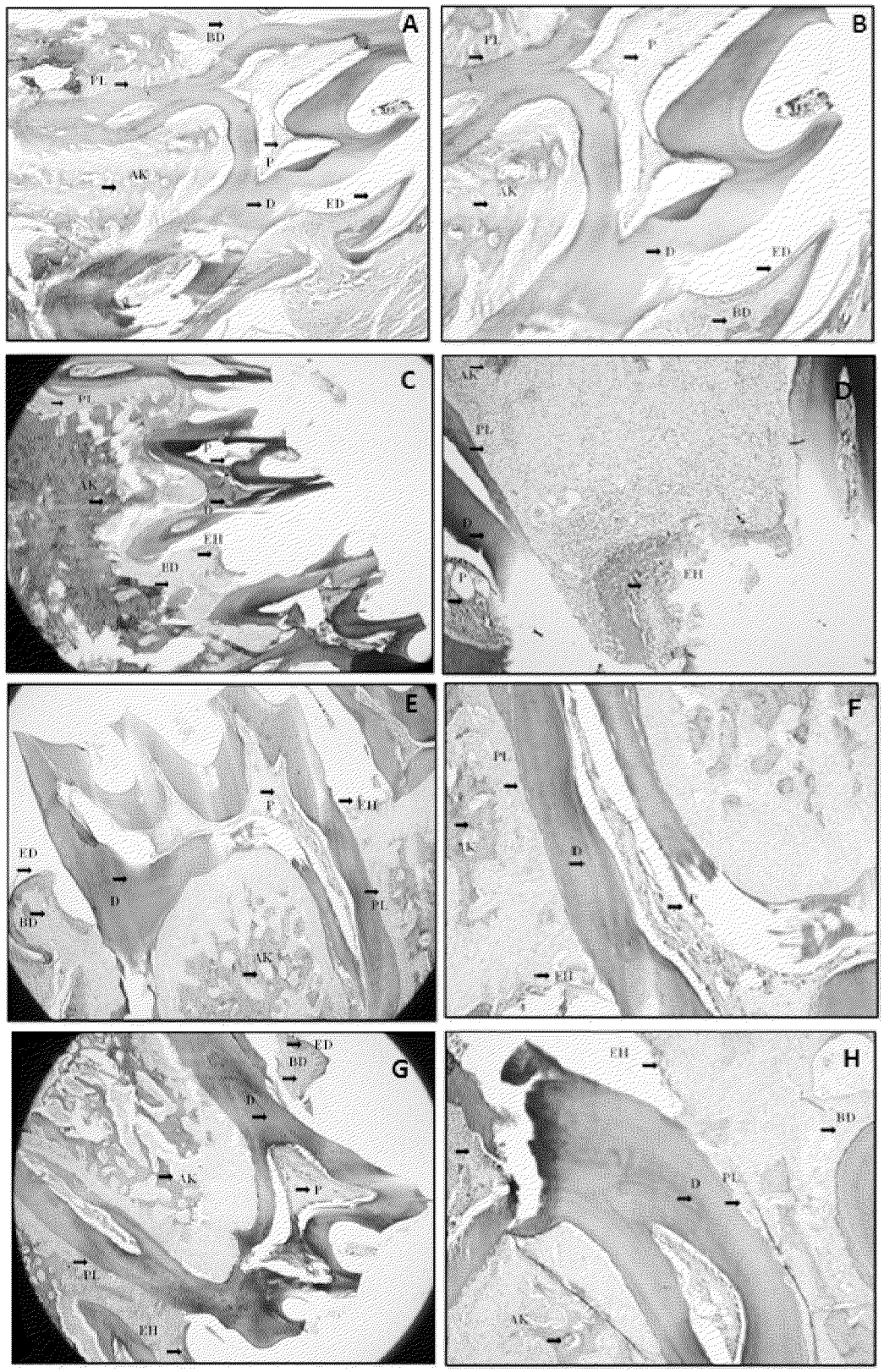
FIG. 3 depicts images of alveolar bone ("AK"), ligament ("BD"), dental ("D"), epithelial tissue ("ED"), inflammatory cells ("EH"), pulpa ("P"), periodontal ligament ("PL"). PANEL (A) shows the control: non-ligated treatment; (HE×40), little visible. PANEL (B) shows the control, non-ligated treatment; (HE×100) no visible ICI. PANEL (C) shows the ligature-only; (HE×40), dense ICI. PANEL (D) shows the ligature-only (HE×100), dense ICI. PANEL (E) shows the ligature plus ASI with a dose of 1.81 mg/kg of diet; (HE×40), slightly visible ICI. PANEL (F) shows the ligature plus ASI with a dose of 1.81 mg/kg of diet; (HE×100) slightly visible ICI. PANEL (G) shows the ligature plus ASI with a dose of 3.62 mg/kg of diet; (HE×40), slightly visible ICI. PANEL (H) shows the ligature plus ASI with dose of 3.62 mg/kg of diet; (HE×100), slightly visible ICI.

FIG. 3 depicts images of alveolar bone ("AK"), ligament ("BD"), dental ("D"), epithelial tissue ("ED"), inflammatory cells ("EH"), pulpa ("P"), periodontal ligament ("PL"). PANEL (A) shows the control: non-ligated treatment (HE× 40). As shown, there was little visible ICI. PANEL (B) shows the control, non-ligated treatment (HE×100). As shown, there was no visible ICI. PANEL (C) shows the ligature-only (HE×40). As shown, there was dense ICI. PANEL (D) shows the ligature-only (HE×100). As shown, there was dense ICI.

PANEL (E) shows the ligature plus ASI with a dose of 1.81 mg/kg of diet (HE×40). As shown, there was less visible ICI. PANEL (F) shows the ligature plus ASI with a dose of 1.81 mg/kg of diet (HE×100). As shown, there was less visible ICI. PANEL (G) shows the ligature plus ASI with dose of 3.62 mg/kg of diet (HE×40). As shown, there was less visible ICI. PANEL (H) shows the ligature plus ASI with dose of 3.62 mg/kg of diet. (HE×100). As shown, there was less visible ICI.

TABLE 4

Bone Mineral Density (BMD)

|  | CONTROL | L | L + ASI I | L + ASI II | P |
|---|---|---|---|---|---|
| BMD (g/cm$^2$) | 0.78 ± 0.03 | 0.77 ± 0.1 | 0.78 ± 0.07 | 0.85 ± 0.06 $^b$ | 0.045* |

Control: the nonligated treatment
L: the ligature-only
L + ASI I: the ligature plus ASI with dose of 1.81 mg/kg of diet
L + ASI II: the ligature plus ASI with dose of 3.62 mg/kg of diet.
*p < 0.05, ** p < 0.01
$^b$ Significant differences from the group as periodontitis.

Figure 4:
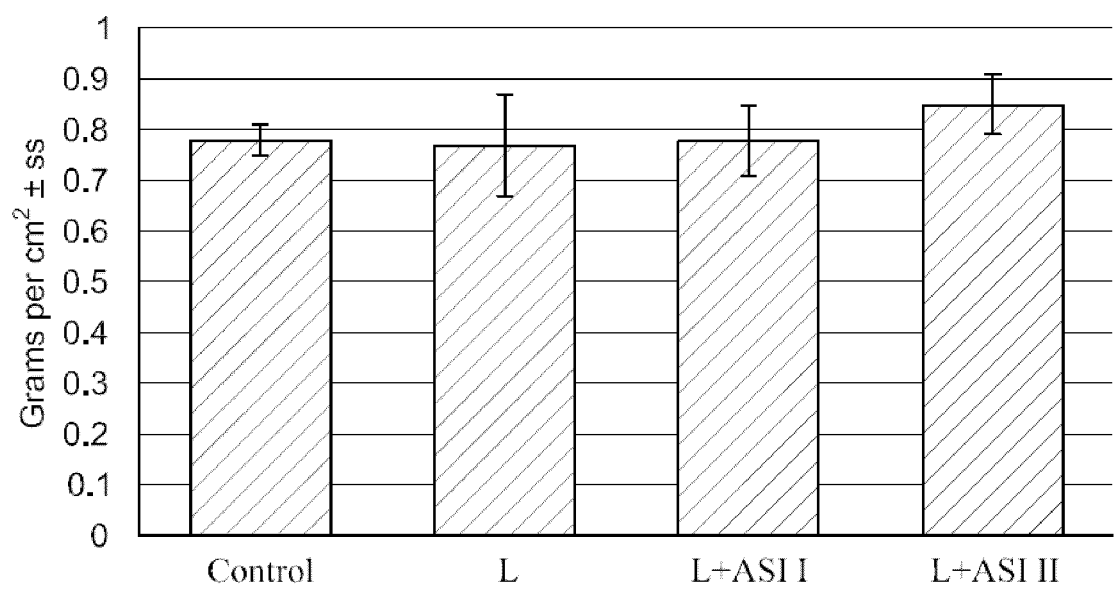
FIG. 4 graphically despicts the bone mineral density results shown in Table 4.

Table 4 shows that bone mineral density was significantly increased in the ASI II with respect to the controls and the ASI I group. The results of Table 4 are graphically depicted in FIG. 4.

TABLE 5

Mean of bone loss parameters

|  | CONTROL | L | L + ASI I | L + ASI II | P |
|---|---|---|---|---|---|
| MCEJ-MCB (mm) | 0.91 ± 0.15 (0.88) | 1.54 ± 0.14 (1.51) [a] | 1.35 ± 0.22 (1.32) [a,b] | 1.39 ± 0.12 (1.40) [a,b] | 0.001** |
| RF-RFCB (mm) | 0.20 ± 0.07 (0.20) | 0.63 ± 0.11 (0.59) [a] | 0.46 ± 0.10 (0.44) [a,b] | 0.53 ± 0.12 (0.54) [a,b,c] | 0.001** |
| DCEJ-DCB (mm) | 0.97 ± 0.37 (1.03) | 1.29 ± 0.24 (1.25) | 1.05 ± 0.21 (1.03) | 1.26 ± 0.28 (1.26) | 0.061 |

Control: the nonligated treatment
L: the ligature-only
L + ASI I: the ligature plus ASI with dose of 1.81 mg/kg of diet;
L + ASI II: the ligature plus ASI with dose of 3.62 mg/kg of diet.
MCEJ: Mesial Cemento-enamel Junction
MCB: Mesial Crestal Bone
DCEJ: Distal Cemento-enamel Junction
DCB: Distal Crestal Bone
RF: Roof of Furcation
RFCB: Roof of Furcation Crestal Bone;
* $p < 0.05$, ** $p < 0.01$
[a] Significant differences from the group as control, ($p < 0.001$).
[b] Significant differences from the group as periodontitis, ($p < 0.001$).
[c] Significant differences from the group as ASI I, ($p < 0.001$).

Figure 5:
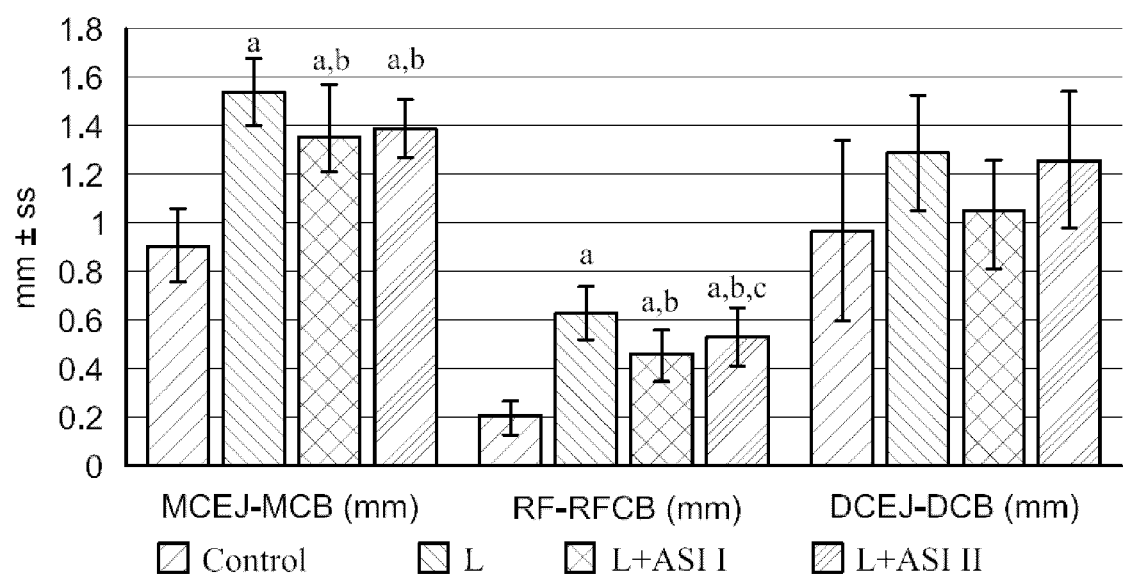
FIG. 5 graphically depicts the mean of bone loss parameter results shown in Table 5 (a—significant differences from the group as control ($p<0.001$); b—significant differences from the group as periodontitis ($p<0.001$); c—significant differences from the group as ASI I ($p<0.001$)).

Table 5 summarizes the mean bone loss results. As shown, mean bone loss between the mesial cemento-enamel junction and the mesial crestal bone was significantly reduced in the treatment groups. Similarly, mean bone loss between the roof of furcation and roof of furcation crestal bone was significantly reduced in the treatment groups. The results are graphically depicted in FIG. 5.

TABLE 6

Rate of bone loss in groups

|  | CONTROL | L | L + ASI I | L + ASI II | P |
|---|---|---|---|---|---|
| MCEJ-MCB/ MCEJ-MRAP | 0.28 ± 0.05 | 0.54 ± 0.04 [a] | 0.49 ± 0.10 [a,b] | 0.50 ± 0.10 [a,b] | 0.001** |
| RF-RFCB/ RF-RFAP | 0.07 ± 0.02 | 0.26 ± 0.05 [a] | 0.21 ± 0.04 [a,b] | 0.22 ± 0.05 [a,b] | 0.001** |
| DCEJ-DCB/ DCEJ-DRAP | 0.32 ± 0.12 | 0.42 ± 0.09 | 0.41 ± 0.12 | 0.42 ± 0.08 | 0.190 |

Control: the nonligated treatment
L: the ligature-only
L + ASI I: the ligature plus ASI with dose of 1.81 mg/kg of diet
L + ASI II: the ligature plus ASI with dose of 3.62 mg/kg of diet.
MCEJ: Mesial Cemento-enamel Junction
MCB: Mesial Crestal Bone
MRAP: Mesial Root Apex
DCEJ: Distal Cemento-enamel Junction
DCB: Distal Crestal Bone
DRAP: Distal Root Apex
RF: Roof of Furcation
RFCB: Roof of Furcation Crestal Bone
RFAP: Roof of Furcation Apex
* $p < 0.05$, ** $p < 0.01$
[a] Significant differences from the group as control, ($p < 0.001$).
[b] Significant differences from the group as periodontitis, ($p < 0.001$).

Figure 6:
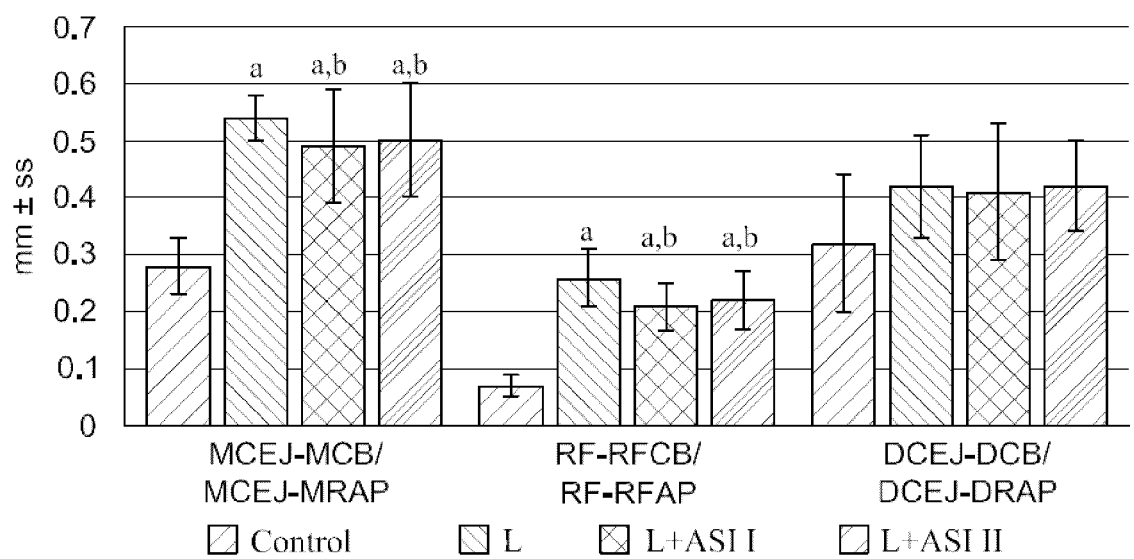
FIG. 6 graphically depicts the rate of bone loss results shown in Table 6 (a—significant differences from the group as control ($p<0.001$), b—significant differences from the group as periodontitis ($p<0.001$))
Figure 7:
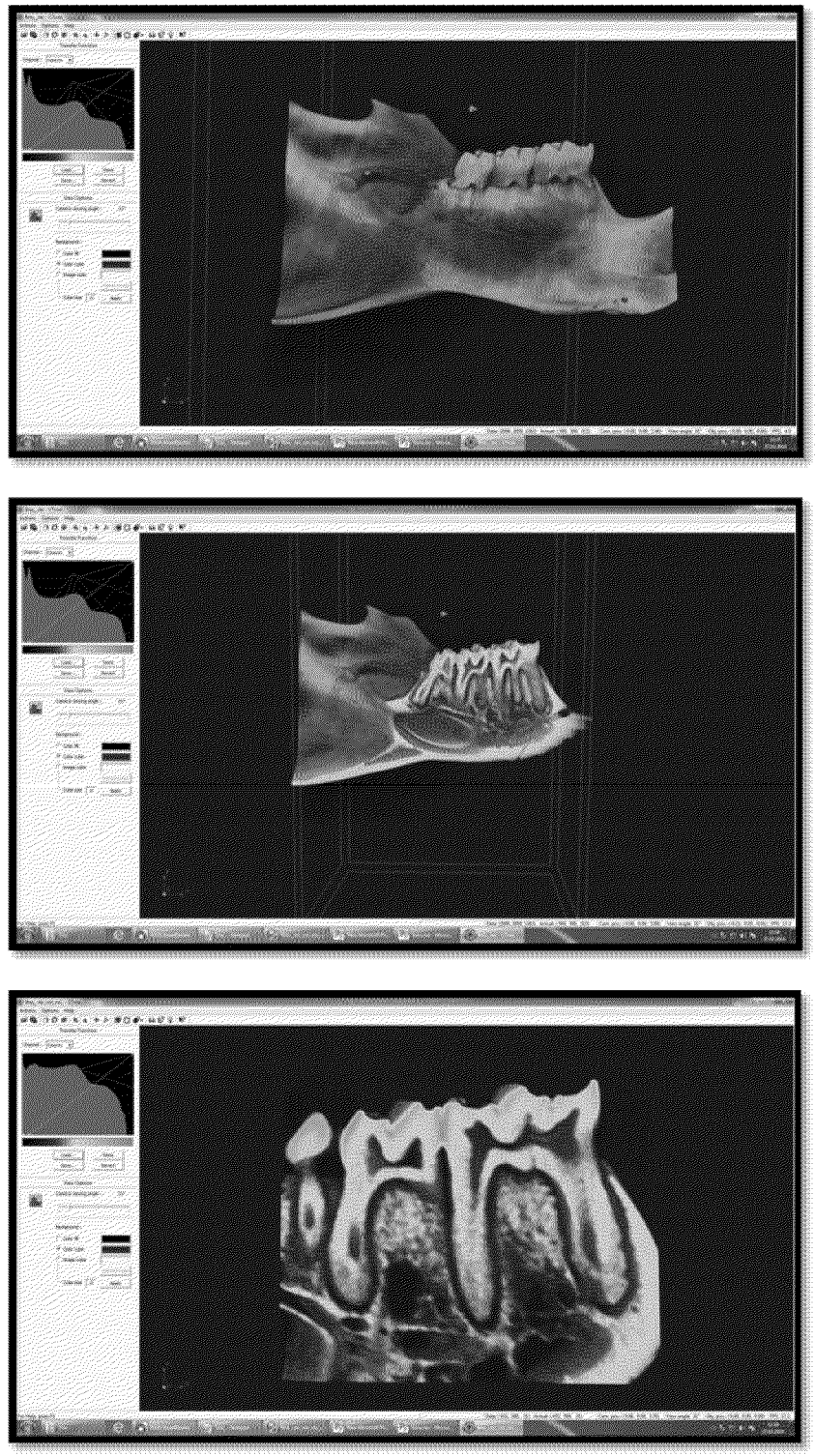
FIG. 7 depicts 3D micro-computed tomography images from the control group.
Figure 8:
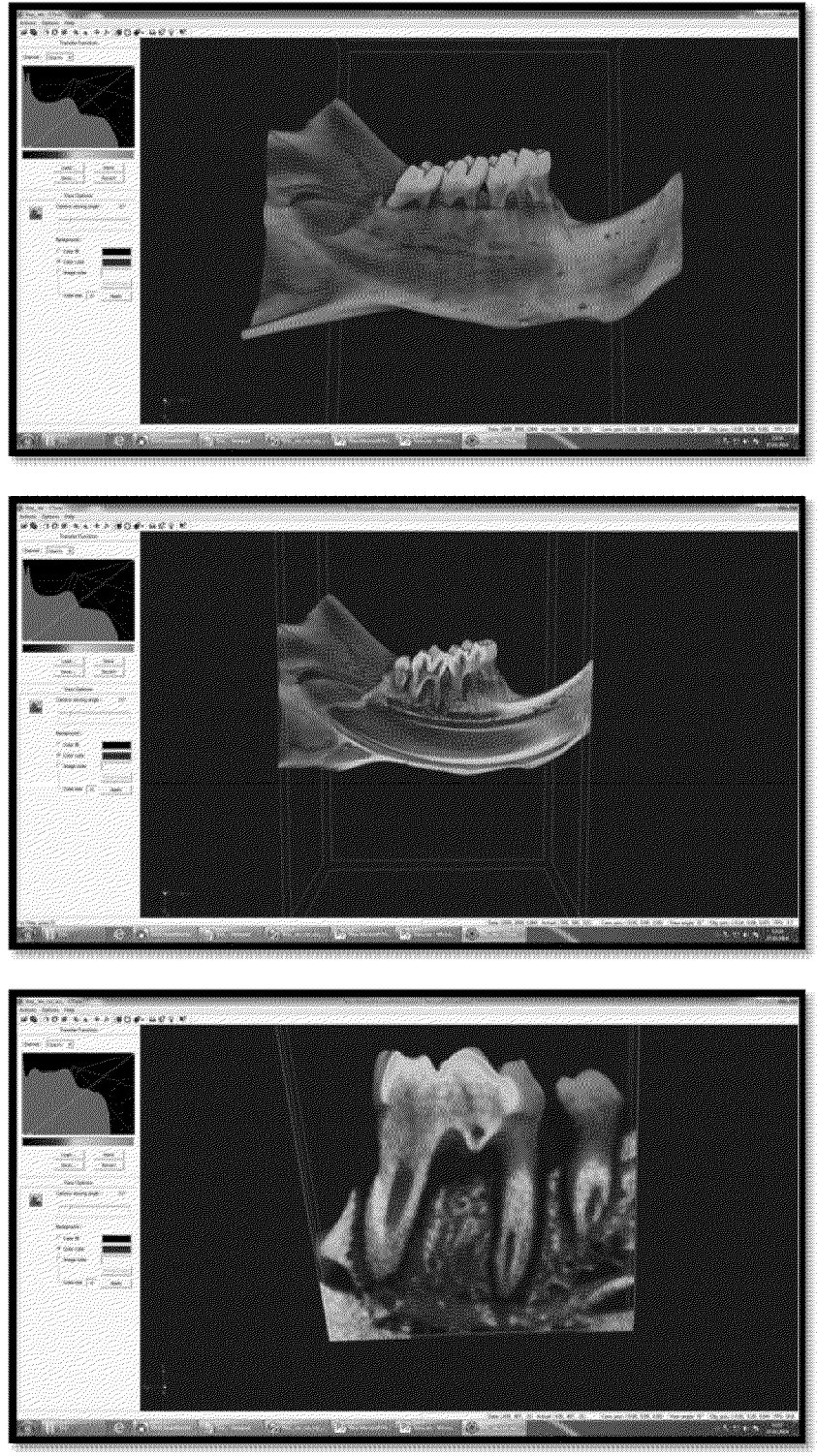
FIG. 8 depicts 3D micro-computed tomography images from the L group.
Figure 9:
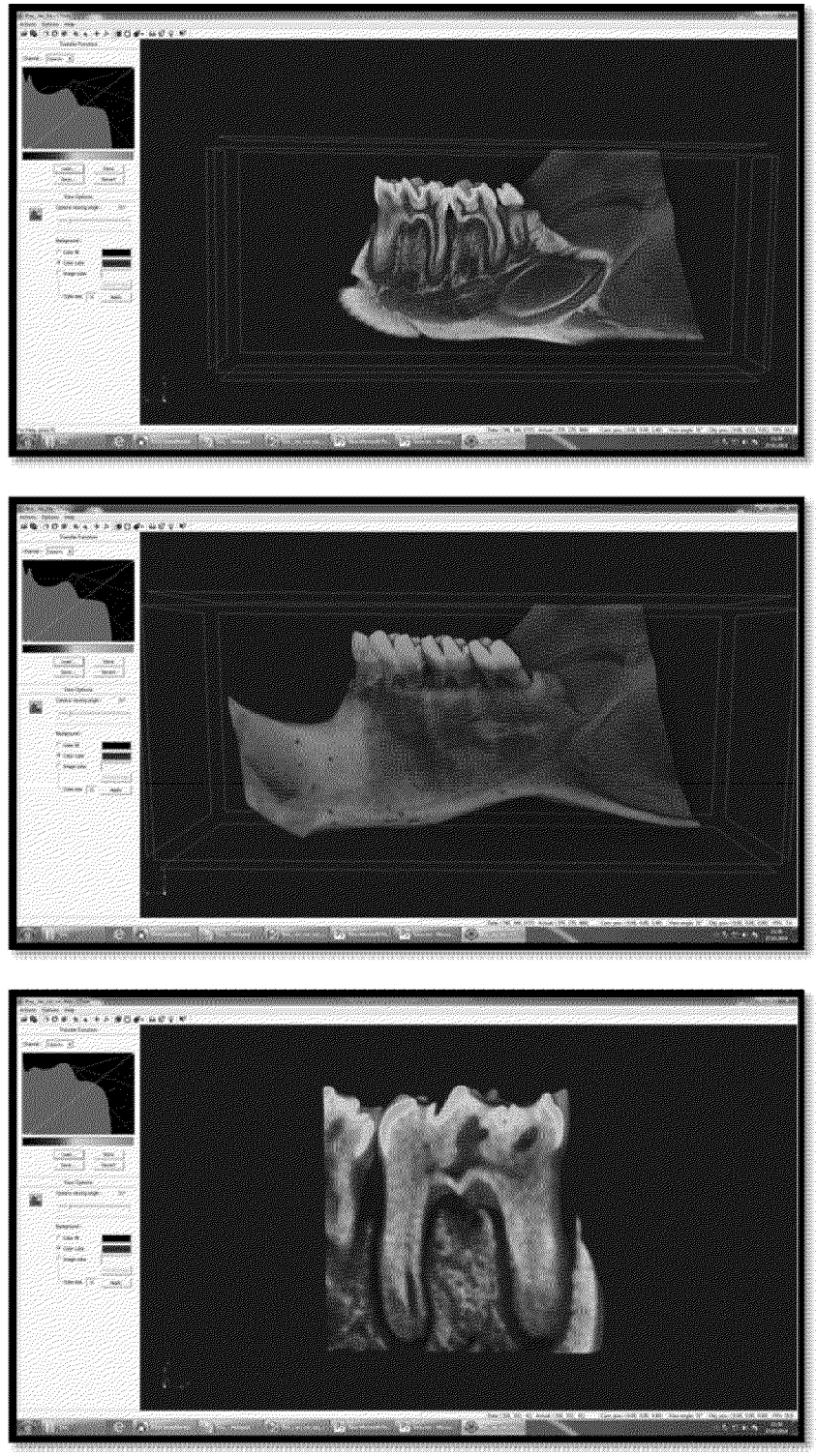
FIG. 9 depicts 3D micro-computed tomography images from the ASI I group.
Figure 10:
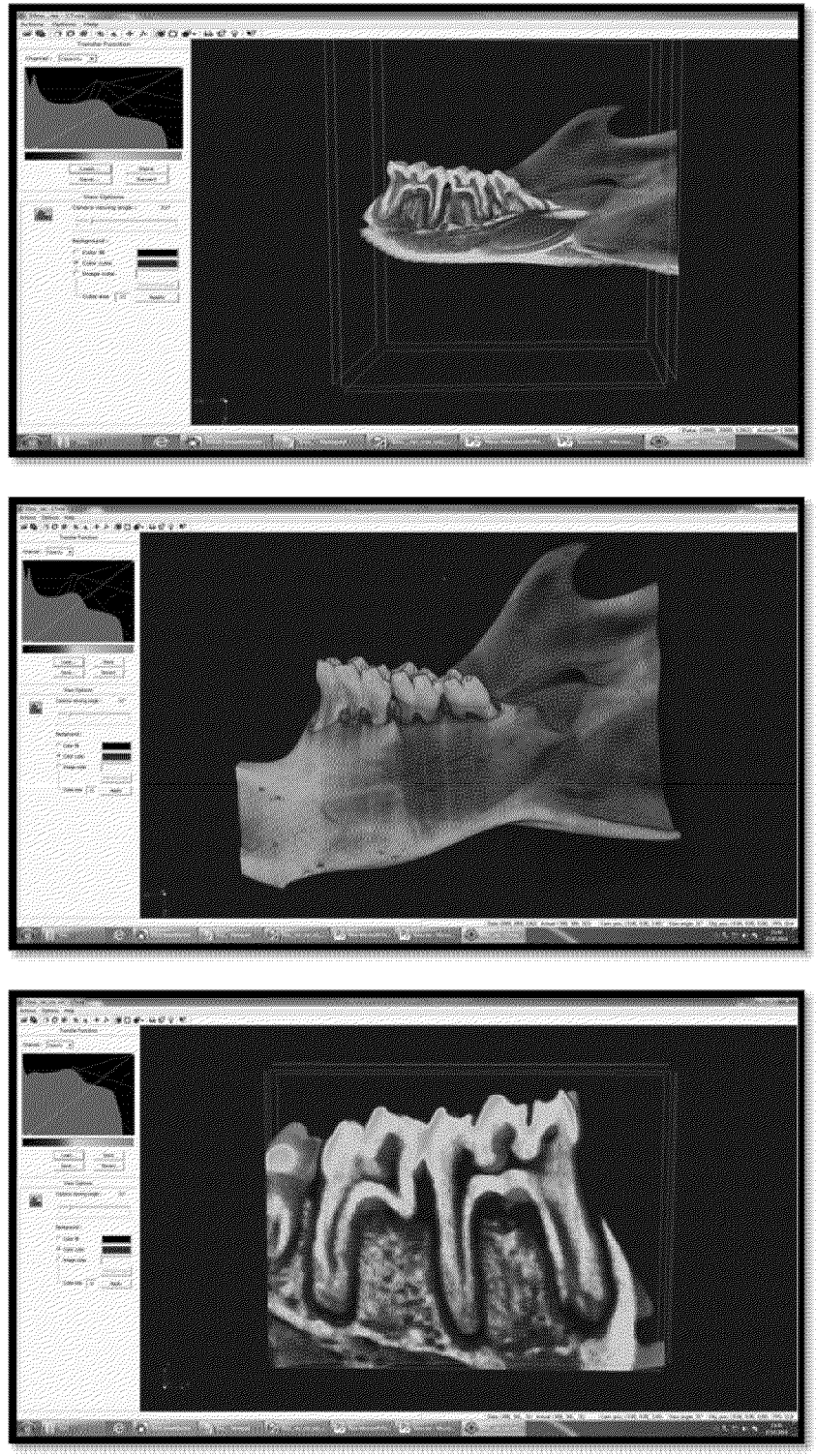
FIG. 10 depicts 3D micro-computed tomography images from the ASI II group.

Table 6 shows the rate of bone loss results. As shown, the rate of bone loss between the mesial cemento-enamel junction and the mesial crestal bone was significantly reduced in the treatment groups. Similarly, the rate of bone loss between the roof of furcation and roof of furcation crestal bone was significantly reduced in the treatment groups. The results are graphically depicted in FIG. 6. FIGS. 7-10 depicts 3D micro-computed tomography images from the control and treatment groups. As shown, there was less visible tooth and bone damage in the treatment groups.

Example 2

The study is a prospective, longitudinal, single-blind pilot intervention trial with six-month follow-up. Subjects presenting with severe or generalized (at least 50% of teeth affected) periodontitis are invited to participate in the study. A baseline visit is conducted by a blind calibrated examiner who collects a complete medical history, standard clinical periodontal parameters and blood samples. Thereafter, patients undergo a standard phase of non-surgical periodontal treatment that is performed by a periodontist. All other necessary dental treatments (extractions of hopeless teeth, restorative treatments) are carried out prior to completion of the periodontal treatment, consisting of oral hygiene instructions and subgingival scaling and root planing.

The therapeutic phase is completed within 1-3 months of the baseline visit. Patients are re-examined at 2 and 6 months after the completion of the treatment. The subjects are divided into three groups based on the baseline visit. Group A includes individuals with marginal (<30%) alveolar bone loss; Group B includes individuals with clinically significant gum recession; and Group C includes individuals with clinically significant enamel erosion. Each group includes 40 individuals, who are subdivided into two control groups (C1 and C2) and two treatment groups (T1 and T2). The treatment protocol is summarized in the table below.

| TREATMENT GROUP | PROTOCOL | RESULTS (AT 3 MONTHS) |
| --- | --- | --- |
| A-T1 | Mouthwash twice daily | Significant reduction in alveolar bone loss |
| A-T2 | Chewie twice daily | Significant reduction in alveolar bone loss |
| A-C1 | Control mouthwash twice daily | No improvement in reducing alveolar bone loss |
| A-C2 | Control chewie twice daily | No improvement in reducing alveolar bone loss |
| B-T1 | Mouthwash twice daily | Halt in gum recession |
| B-T2 | Chewie twice daily | Halt in gum recession |
| B-C1 | Control mouthwash twice daily | Insignificant improvement in reducing gum recession |
| B-C2 | Control chewie twice daily | Insignificant improvement in reducing gum recession |
| C-T1 | Mouthwash twice daily | Halt in enamel erosion |
| C-T2 | Chewie twice daily | Halt in enamel erosion |
| C-C1 | Control mouthwash twice daily | Insignificant improvement in reducing enamel erosion |
| C-C2 | Control chewie twice daily | Insignificant improvement in reducing enamel erosion |

The mouthwash comprises an aqueous solution of arginine silicate and standard orally acceptable excipients. The chewie comprises a butadiene-based polymer and standard orally acceptable excipients impregnated with arginine silicate. The control mouthwash and chewie are identical to the treatment compositions, but lacking arginine silicate.

Example 3

The study group comprises ten systemically healthy subjects with early to mild periodontitis. Patients who have taken antibiotics or received periodontal treatment within 6 months preceding the study are excluded. Prior to any treatment procedure, oral hygiene instructions (OHI) are given. Each quadrant of the subjects is randomly assigned to one of the following groups: (A) scaling and root planning combined with daily administration of arginine silicate post-treatment, (B) scaling and root planning alone, (C) daily administration of arginine silicate alone, and (D) OHI alone.

Subjects are re-examined at one week, four weeks, eight weeks, and 12 weeks. At one week, groups (A)-(C) shows similar improvement in periodontal symptoms, while group (D) shows no significant improvement in periodontal symptoms. At four weeks, Group (A) shows significant improvement in periodontal symptoms, Groups (B) and (C) show minimal improvement in periodontal symptoms, and Group (D) shows no improvement in periodontal symptoms. At eight and twelve weeks, Groups (A) and (C) show significant improvement in periodontal symptoms, Group (B) shows minimal improvement in periodontal symptoms, and Group (D) shows no improvement in periodontal symptoms.

Example 4

20 patients with gingivitis (having at least three of the following symptoms: swollen gums, bright red or purple gum tissue, gum tissue that is sensitive to touch, bleeding gums, bad breath) are studied. Five patients are administered once-daily arginine silicate (I); five patients are topically administered once-daily arginine silicate to the oral cavity (II); five patients are administered chlorhexidine mouthwash for twice-daily use (III); and five patients are administered standard over-the-counter mouthwash for twice daily use (IV).

Patients are evaluated at four weeks, eight weeks, and twelve weeks. At four weeks, groups (I)-(III) have significant reduction in symptoms of gingivitis, while group (IV) has only a minimal reduction in symptoms of gingivitis. At eight and twelve weeks, groups (I) and (II) have the most significant reduction in symptoms of gingivitis, followed by groups (III) and (IV), respectively. The trial is ceased at twelve weeks to avoid side effects from the chlorhexidine treatment. Visible signs of gingivitis decrease significantly. Gum recession is stopped and/or reversed. Bone mineral density in the oral cavity is also increased.

What is claimed is:

1. A method of treating periodontal disease in an individual in need thereof comprising:
   topically administering an effective amount of an arginine-silicate complex to an individual's oral cavity in need of treatment for periodontal disease; wherein the arginine-silicate complex comprises arginine, silicate, and inositol; wherein the effective amount of the arginine-silicate complex is in a toothpaste; and wherein the periodontal disease is selected from the list consisting of gingivitis, periodontitis, tooth decay, enamel erosion and combinations thereof.

2. The method of claim 1, wherein the periodontal disease comprises tooth decay.

3. The method of claim 1, wherein the periodontal disease comprises enamel erosion.

4. The method of claim 1, wherein the periodontal disease comprises gingivitis.

5. The method of claim 1, further comprising the step of identifying an individual in need of treatment for periodontal disease wherein the identifying comprises physical examination by a dental hygienist, dentist, oral surgeon, orthodontist, or medical doctor.

6. The method of claim 1, wherein the effective amount is between about 2 mg and about 2,500 mg.

* * * * *